(12) United States Patent
Mullaney et al.

(10) Patent No.: US 8,334,124 B1
(45) Date of Patent: Dec. 18, 2012

(54) MODIFIED *ASPERGILLUS NIGER* PHYTASE

(75) Inventors: Edward J. Mullaney, Crandon, WI (US); Abul H. J. Ullah, Slidell, LA (US); Xin Gen Lei, Ithaca, NY (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 261 days.

(21) Appl. No.: 12/887,656

(22) Filed: Sep. 22, 2010

Related U.S. Application Data

(60) Provisional application No. 61/244,935, filed on Sep. 23, 2009.

(51) Int. Cl.
*C12N 9/16* (2006.01)

(52) U.S. Cl. .......................... 435/196; 435/15

(58) Field of Classification Search .................... 435/15, 435/196
See application file for complete search history.

(56) References Cited

U.S. PATENT DOCUMENTS

| | | | |
|---|---|---|---|
| 6,638,746 | B2 | 10/2003 | Apajalahti et al. |
| 7,309,505 | B2 | 12/2007 | Lei et al. |
| 2004/0126844 | A1 | 7/2004 | Lei et al. |

OTHER PUBLICATIONS

Kim, Taewan, et al., "Shifting the pH Profile of *Aspergillus niger* PhyA Phytase to Match the Stomach pH Enhances Its Effectiveness as an Animal Feed Additive", Applied and Environmental Microbiology, Jun. 2006, pp. 4397-4403.
Zhang, Wanming, et al., "Adopting Selected Hydrogen Bonding and Ionic Interactions from *Aspergillus funigatus* Phytase Struture Improves the Thermostability of *Aspergillus niger* PhyA Phytase", Applied and Environmental Microbiology, May 2007, pp. 3069-3076.
Berkmen, Mehmet, et al., "The Nonconsecutive Disulfied Bond of *Escherichia coli* Phytase (AppA) Renders It Dependent on the Protein-disulfide Isomaerase, DsbC*", The Journal of Biological Chemistry, vol. 280, No. 12, Issue of Mar. 25, pp. 11387-11394.
Mullaney, Edward J., et al., "The term phytase comprises seeral different classes of enzymes", Biochemical and Biophysical Research Communication, 312, 2003, pp. 179-184.
Ullah, Abul H.J., et al., "Disulfide Bonds are Necessary for Structure and Activity in *Aspergillus ficuum* Phytase", Biochemical and Biophysical Research Communications, 227, 1996, pp. 311-317.

*Primary Examiner* — Tekchand Saidha
(74) *Attorney, Agent, or Firm* — John Fado; Albert Tsui; Lesley Shaw

(57) ABSTRACT

Disclosed herein is site-directed mutagenesis of a cloned phyA gene employed to replaced cysteine residues involved in disulfide bridge formation with another amino acid. Also disclosed herein is an isolated mutant phytase comprising an amino acid sequence having at least 96 percent sequence identity to SEQ. ID. NO: 6 and containing a double-substitution amino acid residue substitution of residue 31 and residue 40 of SEQ. ID. NO: 6, wherein said isolated mutant phytase has phytase activity.

12 Claims, 6 Drawing Sheets

```
                              1         1
MGVEAVLLPLILLSGVTSGLAVPASRNQSSCDTVDQGYQCFSETSHLNQQTAPTTSLANE    60
       2
SVISPEVDAGCRVTFAQVLSRHGARYPTDSRGKKYSALIEHIQQNATFDGKYAFLKTYN   120

YELGADDLTFPGQELVNEGIKFTQRTESLADNIVPFIRSSGSSRVIASGKFIEGFQST   180
                                     3
KLKDPRAQPGQSSPKIDVVISEASSSKNTLDPGTCTVFEDSELADIVEANFTASTVPSIR  240
         4                     4
QRLENDLSGVTLEDTEVTYLMDMCSFDTISTSTVDTELSPFCDLFTHDEVINTDYLQSIK  300

KYYGKEAGNPLGFRQGVGTANELIARLTESPVHDDTSSNHTLDSSPATTFLNGTLYADFS  360
                                                           2
HDKGIISKLPRLGLYNQFKPLSTTTVENTKGTDGFSSANTVPFASRLYVERQCQDASCEP  420
    5    5                             3
LYRVLRRDRVVPLHGCPVDALGRCTEDSFVRCLSPARGGGGKEASCFA
```

SEQ. ID. NO: 6

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
cggaattcct ggcagtcccc g                                           21

<210> SEQ ID NO 2
<211> LENGTH: 24

```
<212> TYPE: DNA
<213> ORGANISM: Artificial Sequence
<220> FEATURE:
<223> OTHER INFORMATION: Primer

<400> SEQUENCE: 2
gctctagact aagcaaaaca ctcc                                          24

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
gagaaatcaa tccagtggcg atacggtcga tcagg                              35

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
aggtgcccgc cggatccaga gtcactttcg c                                  31

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
gacccaggca cctccactgt cttcgaag                                      28

<210> SEQ ID NO 6
<211> LENGTH: 467
<212> TYPE: PRT
<213> ORGANISM: Aspergillus niger

<400> SEQUENCE: 6
```

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

```
Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
            165                 170                 175

Phe Gln Ser Thr Lys Leu Lys Asp Pro Arg Ala Gln Pro Gly Gln Ser
        180                 185                 190

Ser Pro Lys Ile Asp Val Val Ile Ser Glu Ala Ser Ser Ser Asn Asn
    195                 200                 205

Thr Leu Asp Pro Gly Thr Cys Thr Val Phe Glu Asp Ser Glu Leu Ala
210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
450                 455                 460

Cys Phe Ala
465

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
ctacctcatg gacatgggct ccttcgacac c                                    31

<210> SEQ ID NO 8
<211> LENGTH: 33
<212> TYPE: DNA
<213> ORGANISM: Artificial Sequence
```

```
<220> FEATURE:
<223> OTHER INFORMATION: Primer

<400> SEQUENCE: 8
gtcccgctgc atgggggtcc ggttgatgct ttg                              33

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
cgatcagggg tatcaaagct tctccgagac ttcgc                            35

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
cggtcgatca ggggtatcaa tacttctccg agacttcgc                        39
```

MODIFIED *ASPERGILLUS NIGER* PHYTASE

CROSS-REFERENCE TO RELATED APPLICATION

This present application claims priority under 35 U.S.C. §119(e) to U.S. Provisional Ser. No. 61/244,935, which was filed on Sep. 23, 2009, the disclosure of which is hereby incorporated by reference.

FIELD OF THE INVENTION

Disclosed herein is site-directed mutagenesis of a cloned phyA gene employed to replaced cysteine residues involved in disulfide bridge formation with another amino acid. Also disclosed herein is an isolated mutant phytase comprising an amino acid sequence having at least 96 percent sequence identity to SEQ. ID. NO: 6 and containing at double-substitution amino acid residue substitution of residue 31 and residue 40 of SEQ. ID. NO: 6, wherein said isolated mutant phytase has phytase activity.

BACKGROUND OF INVENTION

Presently there are four different classes of enzymes are known to have at least one enzyme member can hydrolyze phytate and release phosphorus. These four classes of phosphatase enzymes are histidine acid phosphatase (HAP), β-Propeller phytase (BPP), protein tyrosine phosphatase (PTP), and purple acid phosphatase (PAP). Out of these four classes, only members of the HAP have been identified has having high specific activity and other features necessary to be marketed commercially. Additionally, only a few HAPs utilize phytic acid effectively as a substrate (Mullaney et al., Inositol phosphates: Linking Agriculture and the Environment 2007, 97-110, Eds B. Turner, A. Richardson, and E Mullaney CABI; Nakaskima et al., Microbial Ecology, (2006) 53:82-88).

Phytase enzymes are a group of histidine acid phosphatases (HAP) with great potential for improving mineral nutrition and protecting the environment from phosphorus pollution coming from animal waste (Lei et al., *J. Appl. Anim. Res.*, 17:97-112 (2000)). *Aspergillus niger* NRRL 3135 phyA phytase has been cloned (Mullaney et al., "Positive Identification of a Lambda gt11 Clone Containing a Region of Fungal Phytase Gene by Immunoprobe and Sequence Verification," *Appl. Microbiol. Biotechnol.* 35:611-614 (1991); and Van Hartingsveldt et al., "Cloning, Characterization and Overexpression of the Phytase-Encoding Gene (phyA) of *Aspergillus niger*," Gene 127:87-94 (1993)) and overexpressed for commercial use as animal feed additive (Van Dijck, *J. Biotechnology* 67:77-80 (1999)). Recent information on its molecular structure from its X-ray-deduced three dimensional structure (Kostrewa et al., "Crystal Structure of Phytase from *Aspergillus ficuum* at 2.5 Å Resolution," Nat. Struct. Biol. 4:185-190 (1997)) has facilitated several studies to enhance the specific activity of other phytases. Analysis of available 3-D structure models of fungal histidine acid phosphatases reveals that disulfide bridges allow for the convergence of distant regions of the amino acid sequence to obtain the required molecular folding of the molecule for specifically function notably at the active site and substrate-binding domain.

Phytase from *Aspergillus fumigatus* has been studied for its superior thermotolerance properties, significant levels of activity over a wide range of pH, and resistance to hydrolysis by pepsin (Pasamontes et al., "Gene Cloning, Purification, and Characterization of a Heat-Stable Phytase From the Fungus *Aspergillus fumigatus*," Appl. Environ. Microbiol. 63:1696-1700 (1997); and Rodriguez et al., "Expression of the *Aspergillus fumigatus* Phytase Gene in *Pichia pastoris* and Characterization of the Recombinant Enzyme," Biochem. Biophys. Res. Commun. 268:373-378 (2000)). However, specific activity of this phytase is not as high as some other fungal phytases such as those produced by *A. terreus* or *A. niger*. As disclosed in Wodzinski, et al., 1996, *Adv Appl Microbiol.*, 42:263-302, wild type strain *A. niger* NRRL 3135 produced the highest yield and activity of phytase. As such, there is a need to further develop an *A. niger* phytase for maintaining activity upon pelletizing temperatures. Ideally, the phytase would be incorporated into animal feed in feed to monogastric animals in a pelletized form.

Given the higher specific activity of *A. niger* phytase, there is a need to explore the role of the disulfide bridge for structural folding and the effect on biological functions. To date, there has been no disclosure reported on the effect of removal of any disulfide bonds in fungal HAPhys.

Studies have reported on the removal of disulfide bridges in *Escherichia coli* HAPhys. Specifically, *E. coli* phytase, AppA, has four disulfide bridges (Lim et al., 2000). Rodriguez et al., Archives of Biochemistry and Biophysics, Volume 382, Issue 1, Pages 105-112 (2000) reported the replacement of one cysteine that was involved in forming a disulfide bridge in *E. coli* phytase, coupled with replacement of other targeted amino acids yielded a phytase with improved thermostability and catalytic efficiency. In another study to define the function of a protein-disulfide isomerase, DsbC, on *E. coli* phytase, a series of phytase mutants lacking either one or both of the cysteines for each of the four disulfide bonds was generated and the phytase produced was characterized (Berkman et al., 2005). While all single *E. coli* mutant phytases displayed lower levels of acid phosphatase activity than the wild type (WT) phytase, one double mutant, C200S C210S, in that study did have higher activity. The degree of loss of activity varied with the cysteine(s) replaced and the results confirmed a relationship between disulfide bridges and catalytic function of the enzyme.

The native NRRL 3135 phyA phytase is a stable enzyme (Ullah et al., "Extracellular Phytase (E. C. 3.1.3.8) from *Aspergillus niger* NRRL 3135: Purification and Characterization," Prep. Boichem. 17:63-91 (1987)) that has a high specific activity for phytic acid (Wyss et al., "Biochemical Characterization of Fungal Phytases (Myo-inositol Hexakisphosphate Phosphohydrolases): Catalytic Properties," Applied and Envir. Micro. 65:367-373 (1999)). This has contributed to its acceptance by the animal feed industry (Wodzinski et al., "Phytase," Advances in Applied Microbiology 42:263-302 (1996)). It has also been widely researched and utilized to engineer improved features into other fungal phytases by recombinant DNA techniques (Wyss et al., "Biophysical Characterization of Fungal Phytases (Myo-iositol Hexakisphosphate Phosphohydrolases): Molecular Size, Glycosylation Pattern, and Engineering of Proteolytic Resistance," Applied and Envir. Micro. 65:359-366 (1999); and Lehmann et al., "Exchanging the Active Site Between Phytases for Altering the Functional Properties of the Enzyme," Protein Science 9:1866-1872 (2000)).

NRRL 3135 PhyA is known to have an active site motif characteristic of the histidine acid phosphatase (HAP) class of enzymes (Ullah et al., "Cyclohexanedione Modification of Arginine at the Active Site of *Aspergillus ficuum* Phytase," Biochem. Biophys. Res. Commun. 178:45-53 (1991); and Van Etten et al., "Covalent Structure, Disulfide Bonding, and Identification of Reactive Surface and Active Site Residues of Human Prostatic Acid Phosphatase," J. Biol. Chem. 266: 2313-2319 (1991)). Previous studies of the crystal structure of the *A. niger* NRRL 3135 phyA (Kostrewa et al., "Crystal. Structure of Phytase from *Aspergillus* ficuum at 2.5 Å Resolution," Nat. Struct. Biol. 4:185-190 (1997)) and phyB (Kostrewa et al., "Crystal Structure of *Aspergillus niger* pH 2.5 Acid Phosphatase at 2.4 Å Resolution," J. Mol. Biol. 288: 965-974 (1999)) molecules have provided researchers with structural models of both these enzymes. These models have facilitated the identification of the residues constituting the catalytic active center of the molecules, i.e., both the active site and substrate specificity site. Its active site consists of a catalytic center (R81, H82, R66, R156, H361 D362) (Mullaney et al., (2000) *Advances in Applied Microbiology* 47:157-199) and a substrate specificity site (K91, K94, E228, D262, K300, K301) (Kostrewa et al., (1999) "Crystal Structure of *Aspergillus niger* pH 2.5 Acid Phosphatase at 2.4 Å Resolution," *J. Mol. Biol.,* 288:965-974). The amino acid numbers refer to full length phytase encoded by the *A. niger* NRRL 3135 phyA gene (NCBI Accession No. AAA32705). Amino acid reference numbers in Kostrewa et al., "Crystal Structure of *Aspergillus niger* pH 2.5 Acid Phosphatase at 2.4 Å Resolution," J. Mol. Biol. 288:965-974 (1999) were derived from a slightly truncated sequence. The narrow substrate specificity and the unique pH activity profile of this phytase, a drop in activity in the pH range 3.0-5.0; have been ascribed to the interaction of these acidic and basic amino acids comprising the substrate specificity site. This low activity at this intermediate pH range is not observed in other fungal phytases and is an undesirable feature of *A. niger* NRRL 3135 phyA.

Phytate (myo-inositol hexakisphosphate) is the major form of phosphorus in plant origin feed. Non-ruminants such as poultry and swine are unable to utilize phytate phosphorus in soy-corn based diet. Supplemental microbial phytase has been used successfully to improve phytate phosphorus utilization and to reduce phosphorus excretion by these animals (Lei et al., "Supplementing Corn-Soybean Meal Diets with Microbial Phytase Linearly Improves Phytate Phosphorus Utilization by Weanling Pigs," J. Anim. Sci. 71:3359-3367 (1993); and Lei et al., "Supplemental Microbial Phytase Improves Bioavailability of Dietary Zinc to Weanling Pigs," J. Nutr. 123:1117-23 (1993)). The most widely used commercial phytase is *Aspergillus niger* PhyA is used as a feed additive. However, PhyA has a unique pH profile of having two pH optima ranges of between 5 to 5.5 and 2.5. A drop in activity exists in the range of pH 3 to 5 with another depression at pH 3.5. Phytate degradation by dietary phytase takes place mainly in the stomach in *Sus scrofa scrofa* (Yi et al., "Sites of Phytase Activity in the Gastrointestinal Tract of Young Pigs," Animal Feed Science Technology 61:361-368 (1996)). Inasmuch as *Sus scrofa scrofa* stomach has pH ranges from 2.5 to 3.5 and there is a depression in PhyA activity at a pH of 3.5 resulting in compromising unmodified PhyA's efficacy for phytase activity. As such there is a need in the art to optimize phytase activity at a range optimal for monogastric animals for in vivo phytate degradation.

Additionally, feed formulations for monogastric animals containing PhyA is heated during a pelletization process. The heat in the pelletization process denatures the enzyme and significantly lowers the activity of the enzyme. Typically, pelletization via a heated extrusion process exposes the feed material to a temperature of approximately 70° C. to 90° C. for a period up to five minutes. As such, there is a need to generate a phytase as an animal feed additive such that the enzyme is heat tolerant and can withstand irreversibly denaturation upon exposure to elevated temperatures.

BRIEF SUMMARY OF THE INVENTION

Disclosed herein is site-directed mutagenesis of a cloned phyA gene employed to replaced cysteine residues involved in disulfide bridge formation with another amino acid. Also disclosed herein is an isolated mutant phytase comprising an amino acid sequence having at least 96 percent sequence identity to SEQ. ID. NO: 6 and containing a double-substitution amino acid residue substitution of residue 31 and residue 40 of SEQ. ID. NO: 6, wherein said isolated mutant phytase has phytase activity. In one embodiment of the invention, the isolated phytase is in a pure or non-pure form. In another embodiment of the invention the isolated mutant phytase is recombinant. In yet another embodiment, amino acid residue 31 is replaced with glycine and residue 40 is replaced by serine. In yet another embodiment of the invention, the phytase maintains phytase activity after being heated to 70° C. In another embodiment of the invention, the phytase retains at least 80% of its phytase activity at a temperature range between 37° C. to 42° C. at a pH of 5.5 subsequent to being heated to 70°. In an embodiment of the invention, the isolated mutant phytase comprises an animal feed composition.

BRIEF DESCRIPTION OF THE DRAWING

FIG. 1 is of the amino acid sequence of *A. niger* NRRL 3135 phytase, Phy A. (NCBI #AAA32705). Pairs of cysteines forming individual disulfide bridges are labeled with matching Arabic numerals.

DETAILED DESCRIPTION OF THE INVENTION

Figure 2:
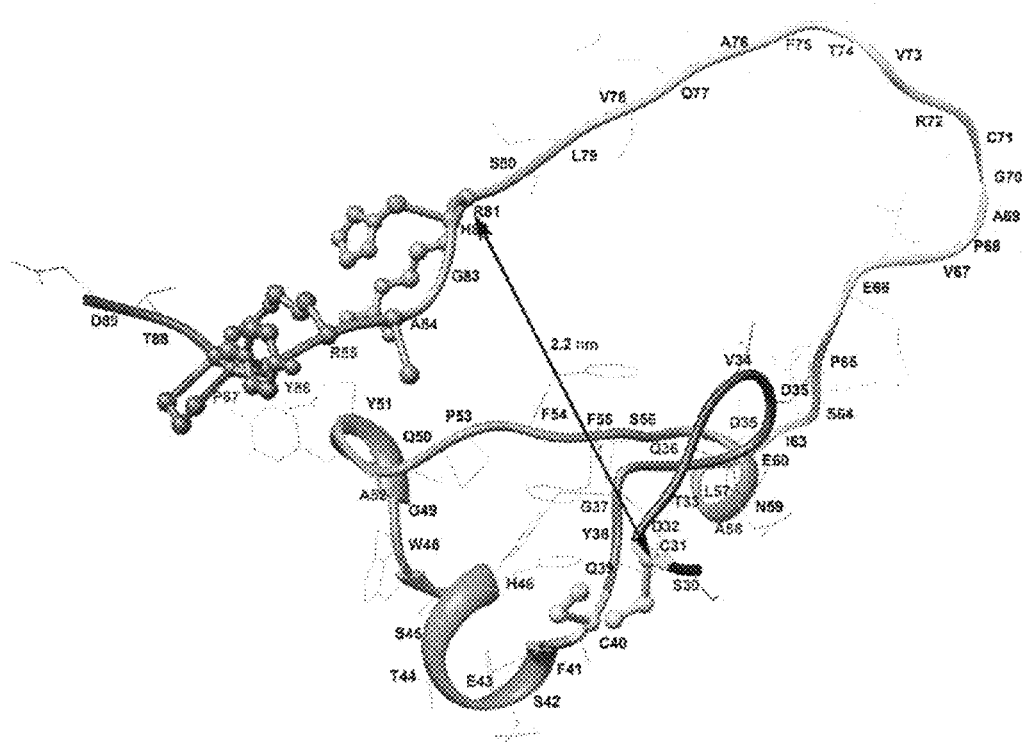
FIG. 2 depicts a molecular model of residue 30 to 89 of *A. niger* Phy A phytase structure. The first disulfide bridge pairs cysteines C31 and C40 and is located towards the N-terminal. The distance between the first disulfide bridge and the beginning of the active site (R81) was computed to be 2.2 nm as indicated with the arrows in the depiction.

The present invention relates to an isolated mutant phytase. In one embodiment of the invention is a mutant phytase having an amino acid sequence having at least 96 percent sequence identity to SEQ. ID. NO: 6, containing at least one substitute of at least one amino acid reside corresponding to residue 31, 71, 215, 264, and 435 in *Aspergillus niger* and *Aspergillus fumigatus*. The isolated mutant phytase can be in pure or non-pure form. The isolated mutant phytase can also be recombinant. In one embodiment of the invention the isolated phytase of is expressed by a *Pitica patoris* strain.

An object of the invention is to disclose a phytase having increased heat tolerance upon an exposure to 70° C. to 90° C. heating process while and still maintaining high phytase activity in the 36° C. to 40° C. range. In another embodiment of this aspect the invention, the mutant phytase of the present invention has an amino acid sequence having at least 96 percent sequence identity to SEQ. ID. NO: 6 and double amino acid substitution at residue 31 and residue 40, wherein the cysteine at residue 31 is replaced with glycine and the cysteine at residue 40 is replaced by serine.

Another object of the invention is that the mutant phytase would maintain high phtyase activity relative to the wild type PhyA after exposure to an elevated temperature range (70° C. to 90° C.) in an extrusion process in producing a pelletized animal feed. In another embodiment of the invention, the mutant phytase of the present invention is incorporated into a pelletized animal feed.

DEFINITIONS

As used in the specification and claims, the singular form "a", "an" and "the" include plural references unless the context clearly dictates otherwise. For example, the term "a cell" includes a plurality of cells, including mixtures thereof.

As referred to herein, SEQ. ID. NO: 6 is the amino acid sequence of the wild type ("WT" or "Wild Type") *Aspergillus niger* phytase (GenBank protein P34752), and has the amino acid sequence as detailed the Sequence listing. As referred herein, "Native PhyA" shall refer to unmodified phytase obtained from *Aspergillus niger* deposited as NRRL 3135.

As described herein, a single amino acid residue substitution can be indicated as follows: the original amino acid residue (expressed as a single-letter abbreviation), followed by the position of the original amino acid residue (i.e., a numerical expression), followed by the new amino acid residue (expressed as a single-letter abbreviation) to be inserted in place of the original amino acid residue. For example, "C31G" means that the original cysteine (C) residue at position 31 is to be replaced by the new glycine (G) residue. For multiple substitutions (e.g., double-substitutions, triple-substitutions, and quadruple-substitutions), the various substitutions are separated by either a slash (/) or by a space. An example of a double-substitution may be expressed as either "C31G/C40S" or as "C31G C40S." In such a double-substitution, there are two mutations: the cysteine residue at position 31 is replaced with a glycine residue, and the cysteine residue at position 40 is replaced with a serine residue.

As a practical matter, whether any particular amino acid sequence having at least 96%, 97%, 98% or 99% identical to, for instance, the amino acid sequence described in SEQ. ID. NO: 6 can be determined conventionally using known computer programs to find the best segment of homology between two sequences. When using sequence alignment program to determine whether a particular sequence is, for instance, 96% identical to a reference sequence according to the present invention, the parameters are set, of course, such that the percentage of identity is calculated over the full length of the reference peptide sequence and that gaps in homology of up to 4% of the total, number of amino acids in the reference sequence are allowed.

Computer-assisted comparison of the disclosed *A. niger* sequence in SEQ. ID. NO: 6 with previously reported sequences present in publicly available databases is useful for identifying functional *A. niger* nucleic acid and polypeptide sequences. It will be understood that protein-coding sequences, for example, may be compared as a whole, and that a high degree of sequence homology between two proteins at the amino acid level indicates that the two proteins also possess some degree of functional homology, such as, for example, among enzymes involved in phytase function.

The present invention also relates to a method of recombinantly producing a mutant phytase. This method involves transforming a host cell with at least one heterologous nucleic acid molecule of the present invention under conditions suitable for expression of the mutant phytase. The mutant phytase is then isolated. Suitable host cells for this method are as described herein (infra).

The present invention further relates to a host cell containing a heterologous nucleic acid molecule of the present invention. The host cell can be a yeast cell or a non-yeast cell. Examples of particular yeast host cells include, without limitation, *Saccharomyces, Kluyveromyces, Torulaspora, Schizosaccharomyces, Pichia, Hansenula, Torulupsis, Candida*, and *Karwinskia*. In another preferred embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera *Pichia, Hansenula, Torulopsis, Candida*, and *Karwinskia*. These yeast genera can use methanol as a sole carbon source. In a more preferred embodiment, the methylotrophic yeast strain is *Pichia pastoris*. Examples of particular non-yeast host cells include, without limitation, bacterial and fungal cells. Suitable examples of non-yeast fungal host cells can include *Aspergillus* species, *Trichoderma* species, and *Neurospora* species.

Methods which are well known to those skilled in the art may be used to construct expression vectors containing sequences encoding phyA and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) Current Protocols in Molecular Biology, John Wiley & Sons, New York, N.Y.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primers a Laboratory Manual*, Cold Spring Harbor Press, Plainview, N.Y.).

A variety of expression vector/host systems may be utilized to contain and express sequences encoding phyA. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CAMV; tobacco mosaic virus, TMV) or with bacterial expression vectors (e.g., Ti or pBR322 plasmids); or animal cell systems.

The invention is not limited by the host cell employed.

"Amino acid sequence" as used herein refers to an oligopeptide, peptide, polypeptide, or protein sequence, and fragment thereof, and to naturally occurring or synthetic molecules. Fragments of phyA are preferably about 467 amino acids in length and retain the biological activity phyA. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

A purified protein or polypeptide of the mutant phytase of the present invention can be obtained by several methods. The purified protein or polypeptide of the mutant phytase of the present invention is preferably produced in pure form (preferably at least about 80%, more preferably 90%, pure) by conventional techniques well known in the art. Typically, the purified protein or polypeptide of the mutant phytase of the present invention is secreted into the growth medium of recombinant host cells. Alternatively, the purified protein or polypeptide of the mutant phytase of the present invention is produced but not secreted into growth medium. In such cases, to isolate the protein or polypeptide of the mutant phytase, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the protein or polypeptide of the mutant phytase of the present invention is subjected to gel filtration in an appropriately sized dextran or polyacrylamide column to separate the proteins. If necessary, the protein fraction (containing the mutant phytase of the present invention) may be further purified by HPLC.

It is contemplated the phytase disclosed herein is utilized as an animal feed additive for monogastric animals that lacking phytase in their digestive tract to hydrolyze phytic acid. Such monogastric animals include, but are not limited to *Sus scrofa scrofa* and *Gallus gallus*.

EXAMPLE 1

Construction of Single Amino Acid Substitution Mutants

Plasmid pYPP1, containing the *A. niger* NRRL3135 phyA gene cloned into the *Saccharomyces cerevisiae* expression vector pYES2 (Han et al., "Expression of an *Aspergillus niger* Phytase Gene (phyA) in *Saccharomyces cerevisiae*," Appl. Environ. Microbiol. 65:1915-1918 (1999), which is hereby incorporated by reference in its entirety), was employed to generate the mutations. Oligonucleotides were synthesized to generate site specific mutations at substrate binding sites described in Table 1. The phyA mutants in pYPP1 were constructed using the Gene Editor in vitro Site—Directed Mutagenesis System according to Mullaney et al., "Site-Directed Mutagenesis of *Aspergillus niger* NRRL 3135 Phytase at Residue 300 to Enhance Catalysis at pH 4.0." Biochem. Biophys. Res. Commun. 277:1016-1020 (2002), which is hereby incorporated by reference in its entirety. The coding region of the pYPP 1 mutant construct was amplified by PCR using two primers (upstream, 5' CGG AAT TCC TGG CAG TCC CCG3' (SEQ. ID. NO: 1); downstream, 5' GCT CTA GAC TAA GCA AAA CAC TCC3' (SEQ. ID. NO: 2)) and inserted into a constitutive expressing vector pGAPZaA (Invitrogen, San Diego, Calif.) at EcoRI and XbaI sites. The gene was led by a signal peptide α-factor and was under the control of GAP promoter. The DNA sequence of each inserted phyA variants was confirmed the presence of the desired mutations in the selected transformants.

Five oligonucleotide primers were employed to generate the necessary mutants, C31G, C71S, C215S, C264G, and C435G (Table 1.) The oligonucleotides were synthesized by Sigma Genosys (Woodlands, Tex.). Mutations were created using thermocyler cycling parameters of: 1 cycle 95° C. for 1 minute and 30 cycles of 95° C. (1 minute), 55° C. (1 minute), 65° C. (10 minutes) and the QuickChange Multi Site-Directed Mutagenesis kit (Strategene, Cedar Creek, Tex.). DNA sequencing to confirm all the mutations was performed with the dye terminator cycle sequencing (DTCS) Quick Start Kit (Beckman Coulter, Fullerton, Calif.) using a CEQ 8000 Genetic Analysis System (Beckman Coulter).

TABLE 1

| Disulfide Bridge | Mutation Substitution | Oligonucleotide primers |
|---|---|---|
| 1 | C310 | SEQ. ID. NO: 3 |
| 2 | C71S | SEQ. ID. NO: 4 |
| 3 | C215S | SEQ. ID. NO: 5 |
| 4 | C264G | SEQ. ID. NO: 7 |
| 5 | C435G | SEQ. ID. NO: 8 |

EXAMPLE 2

Transformation and Protein Expression

The pGAP vector containing phyA mutant gene (10 µg) was linearized by restriction enzyme BamHI and transformed into *Pichia pastoris* X33 by electroporation using ECM 600 Electro Cell Manipulator (Gentronics, Inc., BTX Instrument Division, San Diego, Calif.). The transformed cells were plated in YPD agar (1% yeast extract, 2% peptone, and 2% dextrose) plus zeocin (100 .mu.g/ml) and incubated at 30° C. for 3 days. Single colonies of the transformants were selected, inoculated into YPD media, and incubated at 30° C. for 2 days for phytase expression. Phytase activity of the culture supernatant was measured to screen for high phytase activity-producing transformants or BMGY/BMMY medium for yeast and at 25 µg mL$^{-1}$ to LB for *E. coli*.

Protein Expression

Recombinant yeast strain of *P. pastoris* X33 was used to express proteins identified in Table 1. The pGAP vector containing the phyA gene was linearized by the restriction enzyme BspHI and transformed in *Pichia* cells by electroporation using an ECM 630 Electro Cell Manipulator (Gentronics, Inc., BTX Instructment Division, San Diego, Calif.). The transformed cells were plated on YPD plates plus zeocin and incubated at 30° C. for 3 days. Single colony transformants were then transferred into liquid YPD media at 30° C. for two days and then assayed for phytase activity.

EXAMPLE 3

Phytase Purification

A 500 ml crude culture filtrate of each mutant strain was used to purify the genetically altered phytase. The steps used to purify the protein include ammonium sulfate precipitation followed by three chromatographic steps. Adding 2.0 M HCl while mixing gently lowered to the pH of the culture filtrate from 6.0 to 4.6. Ammonium sulfate precipitation of the phytase was achieved first by saturating the crude culture filtrate to 45% and then removing the precipitate, which does not contain phytase activity, by centrifugation. Additional ammonium sulfate was added to the supernatant to raise the saturation level to 90%. The solution was stirred for about 30 minutes at 40° C. followed by centrifugation to remove the precipitated phytase, which was subsequently dissolved in 15 ml of glycine buffer (25 mM, pH 3.5). The traces of ammonium sulfate were removed from the re-suspended phytase solution by dialysis over a period of 4 hours with three changes of glycine buffer.

A 10 ml UNOsphere S column (2.5×2 cm) was equilibrated in the glycine buffer and the dialyzed protein sample was applied to it at a flow rate of 2.0 ml per min. A linear sodium chloride gradient (0.2 to 1.0 M) was developed in 1.5 minutes using the same buffer. The activity was eluted as a single component. The active fractions were pooled and dialyzed against 25 mM imidazole buffer (PH 7.0). For the second chromatographic step, a 4 ml UNOsphere DEAE column (1.5×203 cm) was equilibrated in the imidazole buffer. The dialyzed protein from the previous step was passed through the column at a flow rate of 2.5 ml per min. A salt gradient (0 to 0.3 M sodium chloride) was developed in 60 ml. Bound phytase activity was eluted as a single component. The active fractions were pooled and dialyzed against the glycine buffer.

A 2 ml UNOsphere S column (1.5×1.2 cm) was equilibrated in glycine buffer. The dialyzed protein from the previous step was applied to this column at a flow rate of 1.5 ml per minute. A linear sodium chloride gradient 0.2 to 0.75 M was developed in 15 minutes in the same buffer. The activity was eluted as a single peak.

EXAMPLE 4

Phytase Activity

Figure 3:
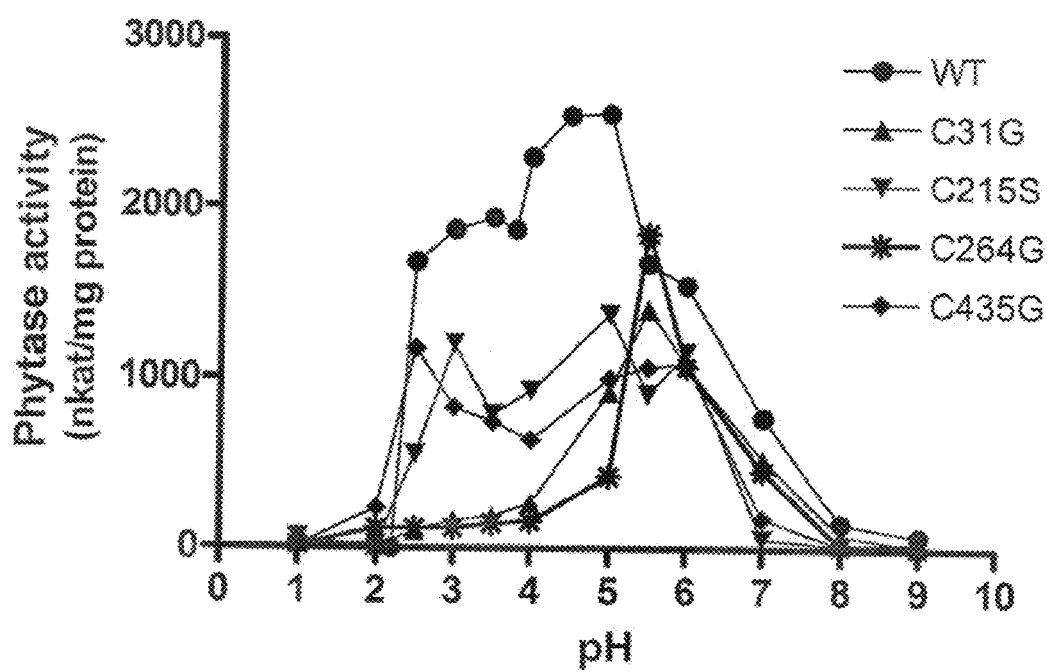
FIG. 3 is a plotted graph comparing pH profiles of wild type and single disulfide bridge mutants with phytases activity expressed at ηmols of ortho-phosphate released per sec) (nKat/mg of protein). Phytase assays were performed at 58° C. for the wild type and at 53° C., 37° C., 37° C., and 42° C. for single substitution *A. niger* mutants of C31, C215S, C264G, and C435G respectively. Mutant C71S did not exhibit phytases activity. The assay buffers were pH 2.0-3.5, 50 mM glycine; pH 4.0 to 5.5, 50 mM sodium acetate; and pH 6.0 to 8.0, 50 mM imidazole.

Phytase assays for single amino acid substitution listed in Table 1 were carried out in 1.0 ml volume at optimum temperatures in 25 mM glycine or 25 mM sodium acetate buffers (Ullah et al., *Preparative Biochemistry and Biotechnology*, Volume 17, Issue 1, pages 63-91 (1987). The liberated inorganic ortho-phosphate was quantitated spectrophotometrically using a freshly prepared acetone-molybdate-acid (AMA) reagent consisting of anhydrous acetone (2 parts), 10 mM ammonium molybdate (1 part), and 2.5 M sulfuric acid (1 part). Adding 2.0 ml of AAM per assay tube terminated the enzyme assay. After 30 seconds, 100 µl of citric acid (1.0 M) was added to each tube to fix the color. Absorbance was read at 355 nm after blanking the spectrophotometer with the appropriate control. Phytase activity was expressed as nKat/ml (nmoles ortho-phosphate released per sec). As indicated in FIG. 3, a substitution of a single disulfide brides resulted in a modification of the of its pH profile.

TABLE 2

| Phytase | $K_m$ (µM) | $K_{cat}$ (sec$^{-1}$) | Kinetic efficiency (mol$^{-1}$ sec$^{-1}$) |
|---|---|---|---|
| WT | 70 | 350 | $5.0 \times 10^6$ |
| C31G | 180 | 234 | $1.3 \times 10^6$ |
| C215S | 145 | 62 | $0.43 \times 10^6$ |
| C264G | 56 | 36 | $0.72 \times 10^6$ |
| C435G | 45 | 90 | $2.0 \times 10^6$ |

EXAMPLE 5 pH Profile

The pH profiles of the expressed phytases listed in Table 1 were determined using the following buffers: 0.2 M glycine-HCl for pH 2-3.5; 0.2 M citrate for pH 4-6.5; 0.2 M Tris-HCl for pH 7-8.5. The substrate was 1% sodium phytase dissolved in each of the selected buffers. Purified enzymes were diluted in nanopure water to give an activity of 0.1 U/ml.

TABLE 3

| Disulfide Bridge | Mutation | Phytase Activity | Optimum Temperature | Optimum pH |
|---|---|---|---|---|
| 1 | C31G | + | 53° C. | 5.5 |
| 2 | C71S | − | — | — |
| 3 | C215S | + | 37° C. | 5.0 |
| 4 | C264G | + | 37° C. | 6.0 |
| 5 | C435G | + | 42° C. | 2.5 |
| Wild Type | | + | 58° C. | 5.0 |

EXAMPLE 6

C31G, C400, C31G/C40G, and C31G/C40S Mutant phytase substitutions

*Escherichia coli* JM 109 cells (Stratagene, Cedar Creek, Tex.) or *E. coli* DH5α competent cells (Invitrogen, San Diego, Calif.) were cultured at 37° C. in LB medium. *Pichia patoris* strain X33 was grown at 30° C. as previously described in Zhang, et al, *Appl. Environ. Microbiol.*, 73:3069-3076 (2007) as incorporated herein by reference. The antibiotic Zeocin (Invitrogen, San Diego, Calif.) was added at 100 µg ml$^{-1}$ to yeast extract-peptone-dextrose (YPD) or BMGY/BMMY medium for yeast and at 25 µg ml$^{-1}$ to LB for *E. coli*. Oligonucleotides were synthesized by Sigma Genosys (Woodlands, Tex.) or Integrated DNA Technologies (San Diego, Calif.). DNA sequencing was preformed with the dye terminator cycle sequencing (DTCS) Quick Start Kit (Beckman. Coulter, Fullerton, Calif.) using a CEQ 8000 Genetic Analysis System (Beckman Coulter) to confirm all the mutations.

A pGAP vector containing the phyA gene as disclosed in Kim et al., *Appl. Environ. Microbiol.*, 72:4397-4403 (2006) was utilized to produce the mutant phytases. Three oligonucleotide primers were employed to generate the necessary mutants, C31G, C40G, C40S (Table 1.) Depending on the oligonucleotide used mutations were created using thermocyler cycling parameters of: 1 cycle 95° C. for 1 minute and 30 cycles of 95° C. (1 minute), 55° C. (1 minute), 65° C. (10 minutes); or 1 cycle 95° C. for 30 seconds and 20 cycles of 95° C. (40 seconds), 60° C. (40 seconds) and 68° C. (5 minutes) and the QuickChange Multi Site-Directed Mutagenesis kit (Strategene, Cedar, Tex.)

Oligonucleotides were synthesized to generate site specific mutations at substrate binding sites described in Table 4. The DNA sequence of each inserted phyA variants was confirmed the presence of the desired mutations in the selected transformants. Transformation, protein expression, and purification techniques were performed in accordance with Examples 2 and 3 listed above.

TABLE 4

| Mutation | Oligonucleotide primers |
|---|---|
| C31G | SEQ. ID. NO: 3 |
| C40S | SEQ. ID. NO: 9 |
| C40G | SEQ. ID. NO: 10 |

EXAMPLE 7 pH Profile of WT, C31G, C40G, C31G/C40G, and C31G/C40S substitutions

Figure 4:
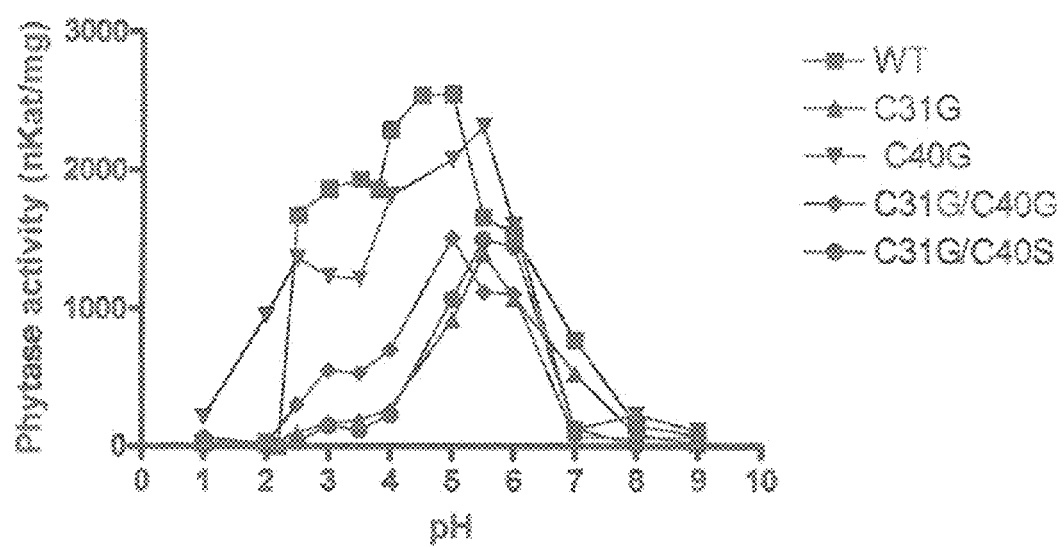
FIG. 4 is a graph comparing phytase activity (nKat/mg) of purified phyA wild type phytase and various disulfide bridge phytase mutants having single and double residue substitutions expressed in *Pichia pastoris* with respect to a pH range. The wild type and mutant phytases were subjected to the optimum temperature for each particular enzyme.

Phytase assays were carried out in 1.0 ml volume at optimum temperatures in 25 mM Glycine or 25 mM sodium acetate buffers as disclosed in Ullah et al., *Preparative Biochemistry and Biotechnology*, Volume 17, Issue 1, pages 63-91 (1987). The liberated inorganic ortho-phosphate was quantitated spectrophotometrically by following the method disclosed in Heinonen et al., *Analytical Biochemistry*, Volume 113, Issue 2, Pages 313-317 (1981) and incorporated herein by reference. Namely the method comprising using acetone-molybdate-acid (AMA) reagent consisting of anhydrous acetone (2 parts), 10 mM ammonium molybdate (1 part), and 2.5 M sulfuric acid (1 part). Adding 2.0 ml of AAM per assay tube terminated the enzyme assay. After 30 sec 100 μl of citric acid (1.0 M) was added to each tube to fix the color. Absorbance was read at 355 nm after blanking the spectrophotometer with the appropriate control. Phytase activity was expressed as nKat/ml (nmoles ortho-phosphate released per sec). The pH profiles were established based on the previously employed method as disclosed in Kim et al., *Appl. Environ. Microbiol.*, 72:43974403 (2006) and incorporated herein by reference. The products of the disulfide bridge mutants were isolated, purified and characterized. The pH profile of each single or double cysteine mutants for the first disulfide bridge are shown in FIG. 4.

EXAMPLE 8

Thermostability of WT, C31G, C40G, C31G/C40G, and C31G/C40S Substitutions

Figure 5:
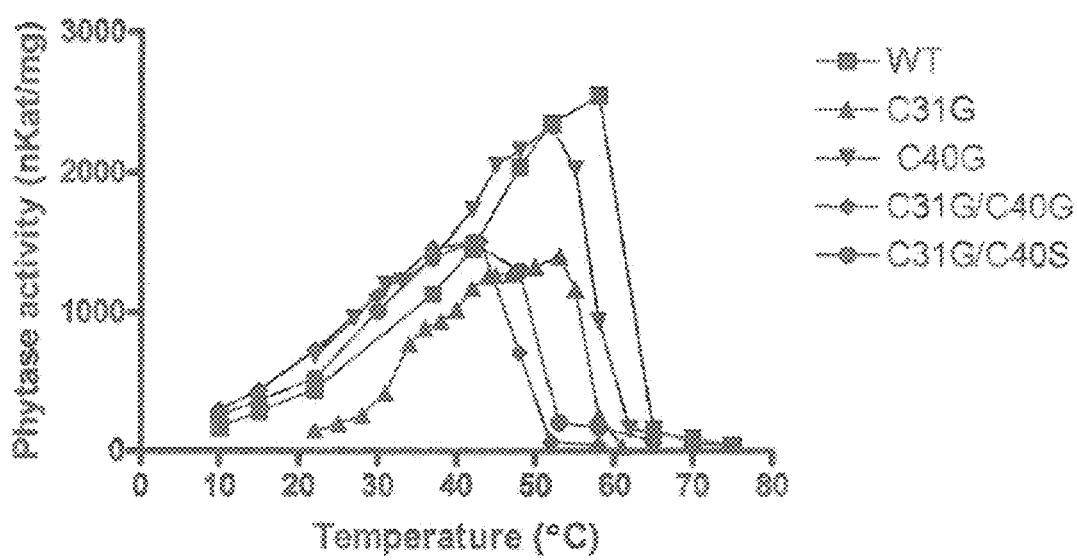
FIG. 5 is a graph depicting phytase activity (nKat/mg) of purified phyA wild type phytase and various disulfide bridge phytase mutants having single and double residue substitutions expressed in *Pichia pastoris* with respect to a temperature range. The phytase subject to the optimum pH for each particular enzyme.

Purified native PhyA and disulfide bridge mutants list in Table 4 with a protein content of 0.4 mg in 1004 were individually sealed in a narrow glass tube with Parafilm and heated at 70° C. for 5 minutes in a water bath. Samples were then equilibrated at room temperature for 10 minutes before placing on ice. The control native PhyA was maintained at room temperature for 5 minutes and not heated to 70° C. before testing. Phytase activity was measure at optimum pH as determined by FIG. 4 of the mutant phytases at 37° C., 42° C., 52° C., and 58° C. The optimum temperature recorded for the disulfide bridge mutants were: C31G 53° C., C40G 52° C., C31G/C40G 42° C., and C31G/C40S 42° C. All the disulfide bridge mutants had a lower optimum temperature than the native PhyA (FIG. 5). In the 36-40° C. temperature range, all DB mutants except for C31G featured higher activity than the WT phytase. The optimum temperature recorded for the DB mutants were; C31G 53° C., C40G 52° C., C31G/C40G 42° C., and C31G/C40S 42° C.

Figure 6:
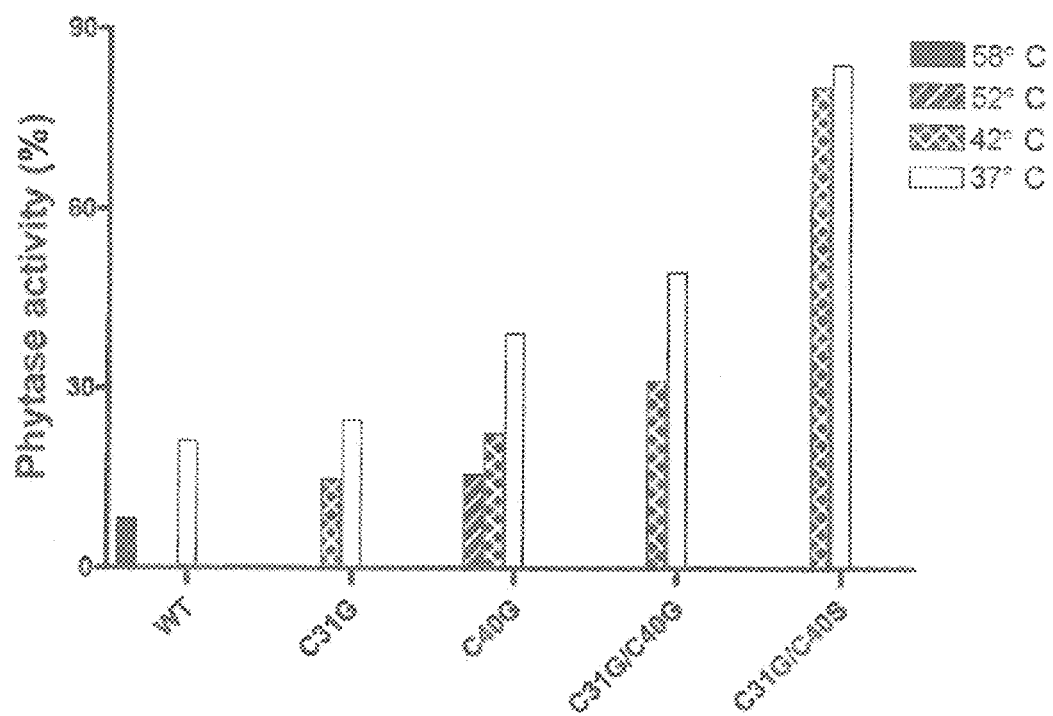
FIG. 6 is graph depicting percentage of phytase activity for wild type derived phyA phytase and various disulfide bridge mutants after an initial 70° C. heat treatment for a period of five minutes followed by activity assays at temperatures of 37° C., 42° C., and 58° C. The pH was adjusted to maximize activity for each particular enzyme.

Notably, and as detailed in FIG. 6, all disulfide bridge mutants retained a higher percentage of activity at 37° C. that the wild type. The 37° C. temperature is important inasmuch as it is represents the physiological internal body temperature of pigs. The disulfide bridge mutants retained a higher percentage of activity at 37° C. than the wild type. Specifically, as noted in Table 5, at 37° C., PhyA showed 21.3% phytase activity, C31G showed 24.8% phytase activity, C40G showed 39.3% phytase activity, 31G/C40G showed phytase activity 49.6%, and C31G/C40S showed 84.2% phytase activity. The double substitution disulfide bride mutants retained more activity than the two single disulfide bridge mutants.

TABLE 5

| Double Mutation | Temperature | ηKat per milliliter before heating | ηKat per milliliter after heating | Retained Phytase Activity % |
|---|---|---|---|---|
| C31G/C40S | 37° C. | 437.2 | 367.9 | 84.2% |
| C31G/C40S | 42° C. | 690.4 | 556.4 | 80.4% |
| C31G/C25G | 37° C. | 367.4 | 182.3 | 49.6% |
| C31G/C25G | 42° C. | 407.7 | 128.3 | 31.4 |
| PhyA | 37° C. | 266.2 | 56.8 | 21.3% |

*pH for the double mutations was at 5.5, the pH for PhyA was at 5.0

The higher heat tolerance of C31G/C40S compared with C31G/C40G also indicates the importance of selecting the replacement amino acid. As such, the replacement of both cysteine pairs in the first DB of *A. niger* PhyA yielded mutants with more desirable attributes for animal feed applications than mutants form replacement of a single cysteine.

While the invention has been described with reference to details of the illustrated embodiment, these details are not intended to limit the scope of the invention as defined in the appended claims.

The embodiment of the invention in which exclusive property or privilege is claimed is defined as follows:

1. An isolated mutant phytase comprising: an amino acid sequence having at least 96 percent sequence identity to SEQ. ID. NO:6 and containing a double-substitution amino acid residue substitution of residue 31 and residue 40 of SEQ. ID. NO:6, wherein said isolated mutant phytase has phytase activity.

2. The isolated phytase according to claim 1, wherein said isolated mutant phytase is in pure or non-pure form.

3. The isolated phytase according to claim 1, wherein said isolated mutant phytase is recombinant.

4. The isolated phytase of claim 3 wherein the phytase is expressed by a *Pichia patoris* strain.

5. The isolated phytase according to claim 1, wherein residue 31 is replaced with glycine and residue 40 is replaced by serine.

6. The isolated phytase according to claim 5 wherein the phytase maintains phytase activity after being heated to 70° C. for approximately 5 minutes.

7. The isolated phytase according to claim 6 wherein the phytase retains at least 80% of its phytase activity at a temperature range between 37° C. to 42° C. at a pH of 5.5 subsequent to being heated.

8. The isolated phytase according to claim 7 wherein the phytase is incorporated into a pelletized animal feed.

9. An animal feed composition comprising the isolated mutant phytase according to claim 1.

10. The animal feed composition of claim 9, wherein the isolated mutant phytase has residue 31 replaced with glycine and residue 40 is replaced by serine.

11. The animal feed composition of claim 10 wherein the phytase maintains phytase activity after being heated to 70° C. for approximately 5 minutes.

12. The isolated phytase according to claim 11 wherein the phytase retains at least 80% of its phytase activity at a temperature range between 37° C. to 42° C. at a pH of 5.5 subsequent to being heated.

* * * * *